United States Patent [19]

Gurtler

[11] 4,273,421

[45] Jun. 16, 1981

[54] SEMICONDUCTOR LIFETIME MEASUREMENT METHOD

[75] Inventor: Richard W. Gurtler, Mesa, Ariz.

[73] Assignee: Motorola, Inc., Schaumburg, Ill.

[21] Appl. No.: 759,618

[22] Filed: Jan. 17, 1977

[51] Int. Cl.³ .............................................. G01N 21/17
[52] U.S. Cl. ..................................... 350/353; 356/433
[58] Field of Search ........................... 350/160 R, 353; 356/432, 433

[56] References Cited

U.S. PATENT DOCUMENTS

| | | | |
|---|---|---|---|
| 3,555,455 | 1/1971 | Paine | 331/94.5 M |
| 4,003,631 | 1/1977 | Biet et al. | 350/160 R |

Primary Examiner—R. A. Rosenberger
Attorney, Agent, or Firm—Paul F. Wille

[57] ABSTRACT

A method for the measurement of minority carrier lifetime in semiconductor wafers, sheets and ribbons by purely optical means. The method does not require electrical or MOS contacts to the wafer, nor does it require any specific processing to facilitate measurement. The technique is non-destructive, and is applicable to any semiconductor wafer, with or without surface dielectric films (e.g., $SiO_2$, $Si_3N_4$, $Ta_2O_5$) as long as it has no metal films. This technique is fast, accurate, and of reasonable high resolution, so that it may be applied to evaluate the effects of specific process steps (e.g., ribbon growth, diffusion, oxidation, ion implantation, delectric deposition, annealing) in real time and hence serve as a production control technique as well as a research tool. By utilizing reasonable equipment sophistication, this technique should enable the measurement of lifetime over a wide range of values, covering the scale from high-speed bipolar devices and integrated circuits ($\sim 10^{-9}$s) to power transistors and solar cells ($\sim 10^{-3}$s).

10 Claims, 1 Drawing Figure

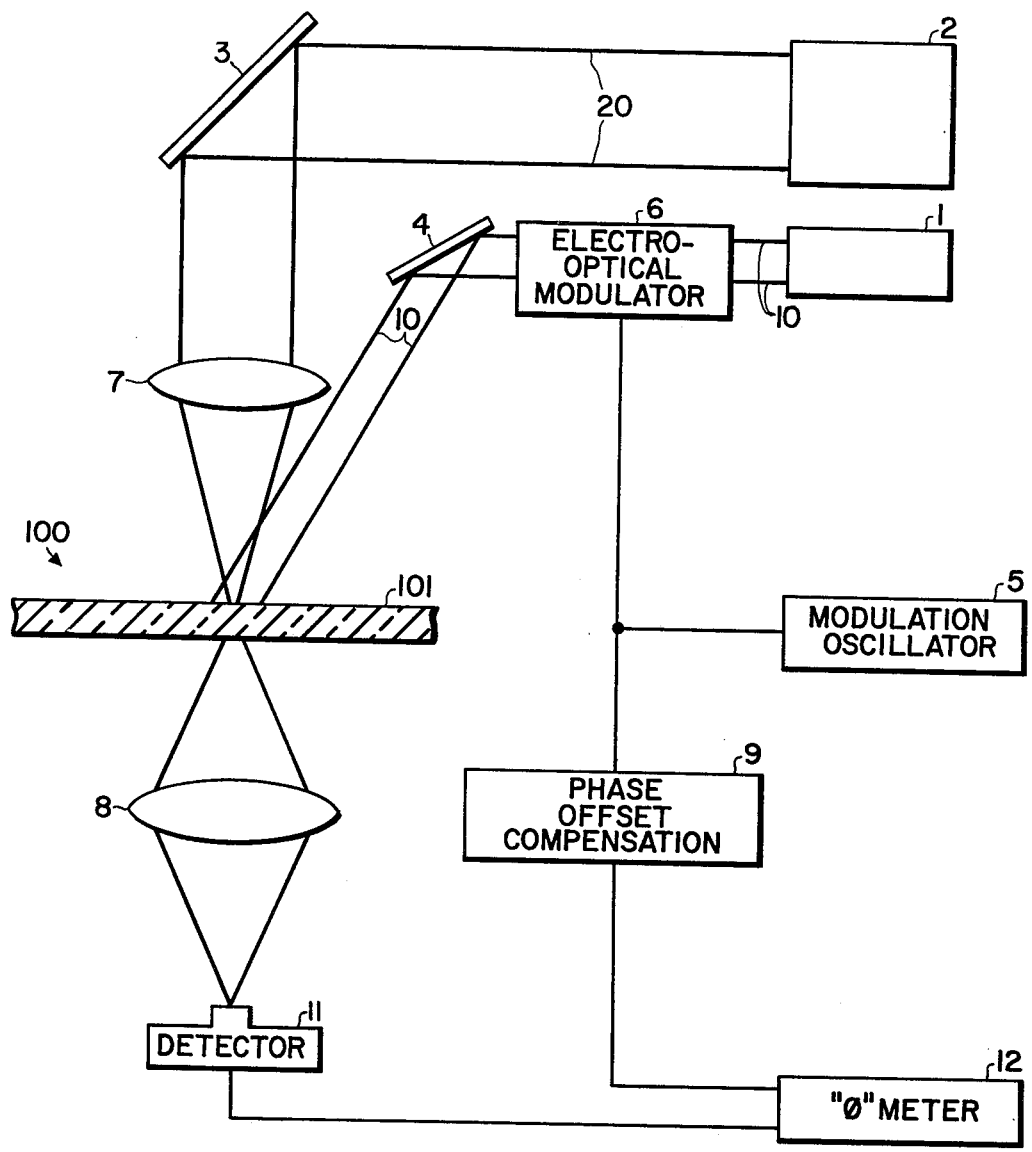

SEMICONDUCTOR LIFETIME MEASUREMENT METHOD

BACKGROUND AND SUMMARY

Semiconductor technology today is highly sophisticated, and in keeping with this high sophistication there is a requirement for rapid diagnostic techniques. In order to optimize a process to obtain best performance from a device (or circuit), it is imperative that diagnostic techniques used be rapid and require little, if any, extraneous processing which can confuse the relevance of the measurement results. Minimal delay between a processing or design change and the measured result of that change is desired so that the information feedback loop can be as rapid as possible.

Minority carrier lifetime is a physical parameter of interest to almost every semiconductor device and materials specialist who wishes to evaluate material quality. A host of techniques is utilized for lifetime measurements at the various stages of semiconductor processing. Some of the more predominant techniques utilized are photoconductive decay, MOS capacitive decay, diode saturation current, diode open circuit voltage decay and SPV (Surface Photo-Voltage) measurements.

Each of these techniques suffers in some way which limits its applicability, and in addition often gives results which can be ambiguous. Photoconductive decay techniques are attractive since little processing is required, although some form of electrical contact is necessary. Unless background lighting is used to fill traps, measurement results can be difficult to interpret. Photoconductive decay is hard to apply to wafers at various stages of processing because of the difficulty of probe contact in anything but coarse geometries. Also, the nature of the contact (Schottky) can influence the results. According to the present invention, an optical beam of sufficient energy to excite free carriers impinges on a localized region of a semiconductor sample. Amplitude modulation of the optical beam results in time-dependent fluctuations of the free carrier density with a phase lag which increases with the free carrier lifetime. Another optical beam with an energy insufficient to excite free carriers but whose absorption depends on the free carrier density passes through the sample including the localized region. This second optical beam is thus amplitude modulated in phase with the free carrier fluctuation; phase comparison of the modulation on both beams is used to calculate the sample lifetime. The accordance with the disclosed invention has the following benefits.

The MOS and diode techniques suffer from requiring processing to be performed on the material. High temperature processing is usually required for the diode techniques, and unless this can be part of a normal processing step, this processing can totally alter the relevance of the measured lifetime. The MOS technique can be performed at lower temperatures if a reasonable electrical contact to the substrate is available. Interpretation of any of these techniques must be carefully done to eliminate surface recombination effects on MOS measurements or junction profile effects on diode measurements.

The SPV technique is distinct in that it actually measures the diffusion length most directly, and indirectly measures the lifetime. In many cases of interest, e.g., solar cells, the diffusion length is the more relevant parameter. This technique however, is indirect in that the absorption coefficient needs to be known accurately, and the degree of strain in the material can alter the absorption coefficients dramatically. In addition, some processing of the wafer is often necessary, and finally, the resolution of the techniques is not good.

All of the above-mentioned techniques have failed to satisfy the need for a fast, reliable technique for lifetime measurement. A new technique is needed and, furthermore, it would seem that only optical techniques can provide a completely in-line, rapid, technique for lifetime measurements.

Lifetime measurements are done optically requiring no contacts or mechanical probing and little, if any, processing is required. Measurements may be made at various processing stages as long as no metalization is present to block the light. Moderate resolution is feasible, e.g., spot sizes of less than 1 mil might be analyzed, depending on various considerations such as optical performance. Very high speed measurements are possible, allowing wafer scanning and tabulation via a data acquisition system.

THE DRAWING

FIG. 1 shows a system for measuring lifetime in a semiconductor sample by the technique to be disclosed.

DESCRIPTION

FIG. 1 is a block diagram of a lifetime mensuration system illustrative of the invention. Sources 1 and 2 provide optical beams 10 and 20 which are made to interact (by means of mirrors 3 and 4 and lens 7) in a localized region of the sample 100; one of the beams generates free carriers while the other beam is not energetic enough to excite free carriers but will interact with the free carriers themselves via free carrier absorption. Designate the more energetic beam as the short wavelength beam 10 and the less energetic or long wavelength beam 20. The beam 20 is chosen to be lightly absorbed by the semiconductor material allowing a significant portion of the beam to be collected by the optical system and detected by the high speed detector. The beam 10 is modulated at a frequency $\omega$ by modulator 6 driven by modulation oscillator 5. The beam 20 will be modulated by the presence of the beam 10 because the beam 10 generates free carriers which in turn partially absorb the beam 20. A modulation signal impressed on the beam 10 will then be measured in the beam 20 detector 11 as a modulation of the beam 20. If a pure sinusoidal modulation at a frequency $\omega$ is used, then this frequency will also be present on the beam 20. However, because of the finite lifetime of the generated minority carriers, the beam 20 will be shifted in phase by the phase angle $\phi$ given by $$\phi = \tan^{-1}(\omega\tau)$$

where $\omega$ is the modulation frequency and $\tau$ is the lifetime. Measurement of $\phi$ at phasemeter 12 in conjunction with phase offset compensator 9 then quite simply gives $\tau$ through $$\tau = \omega^{-1} \tan \phi$$

This comes about because the minority carrier density maximum lags the peak amplitude of beam 10 in a manner dependent on the lifetime. With electronic measurement techniques it is feasible to measure phase angles to better than 0.1 degree; this means that with a single fixed frequency of $\omega = 2\pi \cdot 10^6$ (f=1 MHz), then a lifetime range of $$2.78 \times 10^{-10} < \tau < 9.12 \times 10^{-5} \text{ (Seconds)}$$

may be measured. For longer lifetimes, a correspondingly lower frequency could be used. Similarly, for even shorter lifetimes, higher frequencies can be employed although a practical limit will be reached because: (1) it is difficult to modulate light at frequencies approaching 1 GHz and, (2) the short lifetime means the generated carrier densities are low and, therefore, large intensities are required for a detectable signal—this can cause significant sample heating.

Some theoretical calculations have been made to determine signal levels and the range of applicability of this method. In the simplest, but yet realistic model, the following assumptions are made: The sample 100 is uniform and opaque to the beam 10, i.e., $\epsilon^{-\alpha_s l} \to 0$ where $l$ is the sample thickness and $\alpha_s$ is the constant absorption coefficient for the beam 10. Monochromatic light at wavelength $\lambda_s$ is used. The surface 101 is smooth, characterized by a reflectivity $R_s$ for the beam 10, and a surface recombination velocity s. The lifetime of the bulk of the sample 100 is homogeneous and described by an effective lifetime $\tau$. The incident beam is modulated at a frequency $\omega$ and is of the form $$P_S(t) = \text{Re}\{P_s(1+\eta_s e^{i\omega\tau})\} \text{ (Re=real part of)}$$

where $\eta_s$ is the modulation coefficient ($\eta_s < 1$). $P_s(t)$ is the incident power in watts, over an area A. Trapping effects can be ignored since the average light level, $P_s$, is sufficient to fill all traps in the region of interest. The irradiated region is large compared to a diffusion length in the sample 100 so that no lateral variations are accounted for here. Space charge neutrality is assumed (i.e. $\Delta n = \Delta p$). Surface recombination is assumed constant. With these assumptions, the time dependent continuity equation is, for electrons, $$\partial_t n + \nabla \cdot J_n = G - \frac{n-n_o}{\tau}$$

$$J_n = -D_n \nabla n$$

$$G = \frac{\lambda \alpha_S}{hcA} P_S(x,t) = \frac{\lambda \alpha_s}{hcA} (1-R_s) e^{-\alpha_s x} P_s(t)$$

where G is the carrier generation rate, T is the wavelength of beam 10, h is Planck's constant, c is the speed of light, $n_o$ is the initial nonilluminated carrier concentration, and $D_n$ is the minority carrier diffusion coefficient.

Assuming the diffusion length, $\sqrt{D_n \tau}$, is small compared to the thickness, the boundary conditions under the above assumptions are $$\lim_{x \to l} n(x) = n_o$$

$$D_n \partial_x n|_{x=o} = s(n(o) - n_o)$$

Writing $n(x,t) = n_o + n(x) + \delta n(x) e^{i\omega\tau}$, the solution for this boundary value problem is:

$$\Delta n(x) = \frac{G_o \tau}{1-\alpha_s^2 L_n^2} e^{-\alpha_s x} - \frac{s+\alpha_s D_n}{s+\frac{D_n}{L_n}} e^{-\frac{x}{L_n}}$$

$$\delta n(x) =$$

$$\frac{\eta G_o \tau}{(1-\alpha_s^2 L_n^2)+i\omega\tau} e^{-\alpha_s x} \frac{s+\alpha_s D_n}{s+\sqrt{1+i\omega\tau}\frac{D_n}{L_n}} e^{\sqrt{1+i\omega\tau}\frac{x}{L_n}}$$

where $L_n \equiv \sqrt{D_n \tau}$ $$G_o \equiv \frac{\lambda \alpha_s}{hcA}(1-R_s)P_s$$

Since the effect of interest is the influence of these minority carrier levels on the absorption of the beam 20, these complex spatial distributions may be integrated with the results:

$$\Delta N = \frac{G_o \tau}{\alpha_s} \frac{1-\alpha_s^2 L_n^2 \frac{1+\frac{s}{\alpha_s D_n}}{1+\frac{L_n s}{D_n}}}{1-\alpha_s^2 L_n^2}$$

$$\delta N = \frac{\eta G_o \tau}{\alpha_s(1+i\omega\tau)} \frac{(1+i\omega\tau) - \alpha_s^2 L_n^2 \frac{1+\frac{s}{\alpha_s D_n}}{1+\frac{\sqrt{1+i\omega\tau}}{L_n s} D_n}}{1+i\omega\tau - \alpha_s^2 L_n^2}$$

where $$\Delta N = \int_0^l \Delta n(x) dx, \quad \delta N = \int_0^l \delta n(x) dx$$

It is these total free carrier levels which will affect the beam 20. It can be seen that the application of the beam 10 results in an average carrier level $\Delta N$ which is independent of time, and a time dependent term $\delta N e^{i\omega\tau}$. $\delta N$ is complex, though, and this means that the time dependent term may be written $$\delta N(t) = |\delta N| e^{i(\omega\tau - \Psi)}$$

where $e^{-i\Psi}$ presents the complex phase of $\delta N$. For the general result presented above, the complexity arises due to the bracketed terms. In the ideal case where surface recombination may be assumed negligible these reduce to $$\Delta N = \frac{G_o \tau}{\alpha_s}$$

$$\delta N = \frac{\eta G_o \tau}{\alpha_s(1+i\omega\tau)} = \frac{\eta G_o \tau}{\alpha_s \sqrt{1+(\omega\tau)^2}} e^{-i\phi}$$

$$\phi = \tan^{-1}(\omega\tau)$$

which corresponds to the phase angle cited earlier.

In many cases, it may not be possible to exclude surface recombination effects. In this event, consideration of the effect of s on $\delta N$ must be evaluated since, as can be seen from the expression for $\delta N$, both the amplitude and the phase are affected. To simplify the analysis, it is noted that $\omega$ and $\alpha_s$ are operationally chosen for best measurement purposes while $L_n = \sqrt{D_n \tau}$, $D_n$, and s are material dependent. $\omega\tau$ may (through electronic control) be chosen to be of the order of unity, i.e., $\omega\tau \approx 1$. Then, depending on $\alpha_s$, two special cases can be considered: $\alpha_s L_n \gg 1$ or $\alpha_s L_n \ll 1$. The latter case reduces simply to the ideal case for no surface recombination and reflects the fact that for short diffusion lengths and deep light penetration, surface effects can be ignored.

The case for $\alpha_s L_n \gg 1$ requires more consideration. In this case $\delta N$ becomes $$\delta N = \frac{\delta N_o}{(1 + i\omega\tau)} \left\{ \frac{1 + \frac{s}{\alpha_s D_n}}{1 + \frac{L_n s}{\sqrt{1 + i\omega\tau} \; D_n}} \right\}$$

where $$\delta N_o = \frac{\eta G_o \tau}{\alpha_s}$$

Two extreme cases may now be deduced depending on the magnitude of $L_n s/D_n$:

if $L_n s/D_n \ll 1$, then (1)

$$\delta N = \left[ 1 + \frac{s}{\alpha_s D_n} \right] \frac{\delta N_o}{(1 + i\omega\tau)}$$

$$= \left[ 1 + \frac{s}{\alpha_s D_n} \right] \frac{\eta G_o \tau}{\alpha_s \sqrt{1 + (\omega\tau)^2}} e^{-i\phi}$$

if $L_n s/D_n \gg 1$, then (2)

$$\delta N = \left[ 1 + \frac{s}{\alpha_s D} \right] \frac{D_n}{L_n s} \frac{\delta N_o}{(1 + i\omega\tau)} \sqrt{1 + i\omega\tau}$$

$$= \frac{D_n}{L_n s} \left[ 1 + \frac{s}{\alpha_s D_n} \right] \frac{\eta G_o \tau}{\alpha_s [1 + (\omega\tau)^2]^{\frac{1}{4}}} e^{-i\phi/2}$$

Consequently, in the case $L_n s/D_n \ll 1$, an amplitude change but no additional phase change results. In the second case, $L_n s/D_n \gg 1$, both an amplitude and a phase shift occur, but in this limit the phase change is precisely one-half that expected for an ideal sample.

In the general case, $\Psi$, the phase angle is dependent on s, $\tau$ and $\omega$, i.e., $\Psi = \Psi(s, \tau, \omega)$. This leads to the possibility of determining both s and $\tau$ through curve fitting techniques and measurement of $\Psi(\omega)$ for the particular sample.

Now consider the effects of these carriers on the beam 20. The beam 20 will be attenuated by various mechanisms in its passage through the sample 100 and optical system to the detector. Reflection, scattering, absorption and optical collection efficiencies will be important. If $p_L$ is the incident long wavelength power, then the signal incident on the detector can be written $$P_L = T\gamma P_L$$

where $\gamma$ is an optical collection efficiency and T is the sample transmittance. $\gamma$, as indicated here, is not a fixed constant but can vary depending on surface scattering and this will be an important consideration for rough samples. T will depend on reflection and absorption losses and is of primary interest here. For simplicity, the ideal plane parallel slab of thickness l will be considered first. If a spatially dependent absorption is assumed, then the transmittance, T, and absorption, A, of the plane parallel slab may be found to be $$T = \frac{(1 - R_L)^2 e^{-a}}{1 - R_L^2 e^{-2a}}, \; A = \frac{(1 - R_L)(1 - e^{-2a})}{1 - R_L^2 e^{-2a}}$$

$$\text{where } a = \int_0^l \alpha_L(x) dx$$

and $R_L$ is the long wavelength reflectivity.

The effective absorption parameter, a, will be comprised of various contributions but here we shall simply write $$a = a_I + a_{FC}$$

where $a_{FC}$ represents the absorption parameter due to free carriers while $a_I$ represents that due to other processes. $a_{FC}$ may be written $$a_{FC} = \alpha_e N + \alpha_p P$$

where N and P represent the number of free electrons and holes in the sample and $\alpha_e$ and $\alpha_p$ represent the electron and hole absorption per carrier. Finally, we may write $$a_{FC} = a_o + \Delta a + Re(\delta a)$$

where $$a_o = \alpha_e N_o + \alpha_p P_o$$

$$\Delta a = \alpha_e \Delta N + \alpha_p \Delta P$$

$$\delta a = \alpha_e \delta N e^{i\omega\tau} + \alpha_p \delta P e^{i\omega\tau}$$

However, since space charge neutrality, ($\Delta N = \Delta P$, $\delta N = \delta P$) has been assumed:

$$a_o = \alpha_e N_o + \alpha_e N_o + \alpha_p P_o$$

$$\Delta a = (\alpha_e + \alpha_p) \Delta N$$

Now we may write
$$e^{-a} = e^{-a_I} \cdot e^{-a_o} \cdot e^{-\Delta a} \cdot e^{-a_e - Re(\delta a)}$$

Experimentally assume $\delta a < 1$ and that $e^{-\delta a} \simeq 1 - \delta a$. This leads to $$T = T'(1 - \delta a)$$

$$T' \equiv T(a') \equiv T(a_I + a_o + \Delta a)$$

where T(a') implies evaluation of T for all processes except the time dependent portion. $\delta a$ represents the complex modulation level of the beam 20, i.e., $\eta_L \equiv |-\delta a|$ and $$p_L(t) = p_L(1 - |\delta a| e^{i(\omega t - \Psi)})$$

$$|\delta a| = (\alpha_e + \alpha_p) |\delta N|$$

So finally, for $\delta a \ll 1$, $$p_L(t) = p_L(1 - |\delta a| e^{i(\omega t - \Psi)})$$

$$p_L = \gamma T(a_I, a_o, \Delta a) P_L$$

$$|\delta a| \equiv (\alpha_e + \alpha_p) |\delta N|$$

where $|\delta N|$ and $\Psi$ are obtained from the earlier considerations and T(a') is, for a plane parallel slab, $$T(a') = \frac{(1 - R_L)^2 e^{-a'}}{1 - R_L^2 e^{-2a'}}$$

Consequently, it is seen that the beam 20 incident on the detector is reduced in amplitude by the various absorption, reflection and scattering factors above but is also modulated at a frequency $\omega$ and shifted in phase by $\Psi$.

To demonstrate the feasibility of this technique, utilization will be made of the previous results for the ideal free carrier generation without surface effects and the plane parallel slab model for transmission. For these recall that $$\Delta N = \frac{(1 - R_s)\lambda_s P_s \tau}{Ahc}$$

Similarly $$\delta N = \frac{\eta \Delta N}{\sqrt{1 + (\omega\tau)^2}} e^{-i\phi}$$

The detected signal level will be given by $$\delta P_L = \delta a \, P_L; \quad |\delta \alpha| = (\alpha_e + \alpha_p) |\delta N|$$

$$\delta P_L = (\alpha_e + \alpha_p) \frac{\eta \Delta N}{\sqrt{1 + (\omega\tau)^2}} e^{-i\phi} \gamma T P_L$$

where $T = \dfrac{(1 - R_L)^2 e^{-a'}}{1 - R_L^2 e^{-a'}}$

As an example, assume the parameters indicated below:

$n_o = 10^{16} \text{cm}^{-3}$    $\omega = 2\pi \cdot 10^6 \text{sec}^{-1}$
$l = .05 \text{cm}$    $\eta_s = .5$
$\lambda_L = 10.6 \mu\text{m}$    $\alpha_e \simeq \alpha_p \simeq 10^{-16} \text{cm}^2$
$\lambda_S = .6 \mu\text{m}$    $\gamma = .9$
$R_L = .29$    $P_s = 100 \text{mw over 1mm}^2$
$R_S = .35$    $P_L = 100 \text{mW over 1mm}^2$
$\tau = 10^{-7} \text{sec}$
then
$\Delta N = 1.96 \cdot 10^{12} \text{cm}^{-2}$    $a_o = .05$
$|\delta N| = 8.29 \cdot 10^{11} \text{cm}^{-2}$    $\Delta a_o = 3.92 \cdot 10^{-4}$
$\phi = 32°$    $T = .52$
$|\delta \alpha| = 1.66 \cdot 10^{-4}$    $\delta P_L = 7.75 \mu W$
$N_o = 5.10^{14} \text{cm}^{-2}$    $P_L = 46.7 \text{mW}$ Therefore, under these conditions, a modulation of $1.66 \cdot 10^{-4}$ results in a signal level of 7.75 $\mu$W riding on a static 46.7 mW level. A phase shift of 32° will result.

Based on the foregoing considerations, the following gives details of specific means contemplated for implementing the lifetime measurement. Beam 20 is about 1 cm wide and has a 10.6$\mu$ micron wavelength supplied by a $CO_2$ laser 2 at a 0.1–1 W power level $P_L$. The beam 10 is about 1 mm wide and has a 0.628 micron wavelength supplied by a HeNe laser at a 0.1–1 w power lever $P_S$. Lens 7 and 8 are Zn-Se with a 2.5 inch focal length. Detector 20 is a cooled high-sensitivity Hg-Cd-Te unit. Amplification and phase comparison are effected by a Princeton Applied Research Model 124 lock-in amplifier. Beam 10 is modulated by a high-speed chopper or accoustic modulator.

While many variations on the above elements are obviously possible, what is claimed is:

1. A method for measuring semiconductor lifetime comprising:
   generating free carriers in a region of the semiconductor with a first modulated optical beam;
   modulating a second optical beam with said free carriers;
   detecting the modulation of said second optical beam;
   comparing the phase of the detected modulation of said second optical beam with the modulation of said first modulated optical beam; and
   calculating the lifetime of said free carriers from said compared phase and the frequency of modulation of said first modulated optical beam.

2. The method of claim 1 where said modulation has a frequency much less than that of said optical beams.

3. The method of claim 1, where said region is a surface region.

4. The method of claim 1, where said second optical beam passes entirely through said semiconductor.

5. The method of claim 1, where said second optical beam passes entirely through said semiconductor.

6. The method of claim 1, where said phase comparison is accomplished by electronic means.

7. The method of claim 1, where said second optical beam has a larger wavelength than said modulated optical beam.

8. The method of claim 1, where said phase comparison is accomplished at each of at least two modulation frequencies.

9. The method of claim 8, further including calculating the surface recombination velocity.

10. The method of claim 1, further including calculating the surface recombination velocity.

* * * * *